(12) United States Patent
Elsen-Wahrer et al.

(10) Patent No.: US 10,004,673 B1
(45) Date of Patent: Jun. 26, 2018

(54) HAIR TREATMENT COMPOSITION COMPRISING MICHAEL ADDITION PRODUCT AND METHODS FOR TREATING HAIR

(71) Applicant: L'OREAL, Paris (FR)

(72) Inventors: Andrea Elsen-Wahrer, Linden, NJ (US); Jim Singer, South Orange, NJ (US)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 15/427,488

(22) Filed: Feb. 8, 2017

(51) Int. Cl.
| | |
|---|---|
| A61Q 5/12 | (2006.01) |
| A61K 8/45 | (2006.01) |
| A61K 8/41 | (2006.01) |
| A61K 8/37 | (2006.01) |
| A61K 8/23 | (2006.01) |
| A61K 8/22 | (2006.01) |
| A61Q 5/00 | (2006.01) |
| A61Q 5/08 | (2006.01) |

(52) U.S. Cl.
CPC ............. *A61K 8/45* (2013.01); *A61K 8/22* (2013.01); *A61K 8/23* (2013.01); *A61K 8/37* (2013.01); *A61K 8/41* (2013.01); *A61Q 5/004* (2013.01); *A61Q 5/08* (2013.01); *A61Q 5/12* (2013.01); *A61K 2800/5922* (2013.01); *A61K 2800/88* (2013.01)

(58) Field of Classification Search
CPC ... A61K 8/45; A61K 8/22; A61K 8/37; A61K 2800/41; A61K 2800/5922; A61Q 5/08; A61Q 5/12
USPC ...................................................... 424/70.1
See application file for complete search history.

(56) References Cited

U.S. PATENT DOCUMENTS

| | | | | |
|---|---|---|---|---|
| 4,863,993 A | * | 9/1989 | Montgomery | A61K 8/37 524/317 |
| 5,501,851 A | | 3/1996 | Mudge et al. | |
| 6,610,759 B1 | | 8/2003 | Chappelow et al. | |
| 8,901,199 B2 | | 12/2014 | Vu et al. | |
| 2003/0100694 A1 | | 5/2003 | Holguin | |
| 2013/0263875 A1 | | 10/2013 | Burgess et al. | |
| 2014/0234239 A1 | | 8/2014 | Sirdesai | |
| 2014/0234240 A1 | | 8/2014 | Sirdesai | |
| 2014/0242011 A1 | | 8/2014 | Sirdesai | |
| 2014/0335032 A1 | | 11/2014 | Panandiker et al. | |
| 2015/0099076 A1 | | 4/2015 | Smets et al. | |
| 2015/0359724 A1 | | 12/2015 | Ijdo et al. | |
| 2016/0067164 A1 | | 3/2016 | Valia et al. | |
| 2016/0296455 A1 | | 10/2016 | Kergosien et al. | |
| 2016/0296456 A1 | | 10/2016 | Kergosien et al. | |
| 2016/0303029 A1 | | 10/2016 | Kergosien et al. | |

FOREIGN PATENT DOCUMENTS

| | | |
|---|---|---|
| JP | H-05163118 A | 6/1993 |
| JP | H-11071240 A | 3/1999 |
| JP | H-11071241 A | 3/1999 |
| WO | WO-0025697 A1 | 5/2000 |
| WO | WO-2016/160796 A1 | 10/2016 |

OTHER PUBLICATIONS

STIC Search Report dated Jul. 17, 2017.*

* cited by examiner

*Primary Examiner* — Eisa B Elhilo
(74) *Attorney, Agent, or Firm* — Polsinelli PC (L'Oreal USA)

(57) ABSTRACT

The present disclosure relates to hair care compositions such as hair restructuring compositions comprising a combination of restructuring components. The compositions are unique because they dramatically improve the quality and durability of hair, especially chemically treated hair. Typically, the compositions include: (a) one or more amines selected from the group consisting of diamines, polyamines, alkylamines, alkanolamines, and mixtures thereof; (b) one or more unsaturated carboxylic acids of formula (I):

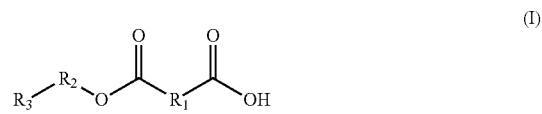

(I)

wherein $R_1$ is a linear or branched $C_2$-$C_{10}$ alkenyl group; $R_2$ is a linear or branched $C_1$-$C_{10}$ alkyl group; and $R_3$ is (meth)acryloyloxy; and (c) a cosmetically acceptable carrier.

18 Claims, No Drawings

HAIR TREATMENT COMPOSITION COMPRISING MICHAEL ADDITION PRODUCT AND METHODS FOR TREATING HAIR

FIELD OF THE DISCLOSURE

The present disclosure relates to compositions and methods for treating hair, kits comprising the compositions, and methods for using the compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades. The process of lifting the color of hair, also known as lightening (or bleaching), generally requires the use of oxidizing agents. Lightening of hair is typically evaluated by the variation in tone height before and after the application of a hair color-altering composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels can range from 1 (black) to 10 (light blond), one unit corresponding to one tone; thus, the higher the number, the lighter the shade or the greater the degree of lift.

In general, hair lightening or color lifting compositions and hair coloring or dyeing compositions possess an alkalinity such that these compositions have a pH value of above 7, typically being at pH 9 and above, and may generally require the presence of an alkalizing agent such as ammonia or an ammonia gas generating compound and/or an amine or ammonium-based compound in amounts sufficient to make such compositions alkaline. The alkalizing agent causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effective alter the shape of the hair, these chemical treatments can damage the hair fibers and/or irritate the scalp. Thus, in order to reduce or avoid damage to hair, as well as to improve the cosmetic performance of the compositions, the use of new and additional components and novel combinations of ingredients are continuously sought.

However, the choice of components or combinations of ingredients could pose difficulties insofar as they cannot be detrimental to other cosmetic attributes such as ease and uniformity of application, rheology or viscosity properties and stability of the compositions, color deposit and target shade formation, and/or result into more disadvantages such as increased damage or a less healthy look to the hair. It would therefore be desirable to provide the consumer with compositions and methods that can chemically treat the hair while providing other cosmetic advantages such as shine, conditioning, fiber strength, and/or a healthy appearance to the hair, but avoiding or minimizing damage to the hair.

Further, both natural and sensitized or chemically treated hair can contain several kinds of negatively charged moieties, for example, carboxylates (resulting from the hydrolysis of amino acids and thioester bonds) and/or sulfonates (resulting from the oxidation of disulfide bonds). These negatively charged moieties can degrade the cosmetic properties of the hair. Moreover, when hair is chemically treated or damaged, the disulfide bonds in hair (disulfide linkages between two cysteine units) can be reduced or broken, resulting in the formation of thiol groups and/or cysteic acid.

Thus, one objective of the disclosure is to provide novel compositions that can provide advantageous effects such as strengthening of the hair fiber, protecting hair fibers from damage or further damage, enhanced properties such as softness, shine, conditioning, healthy appearance, while at the same time, providing desired effects such as coloring, lightening, straightening, relaxing, and/or shaping.

SUMMARY OF THE DISCLOSURE

The present disclosure relates to compositions and methods for treating hair, in particular human hair of the head. The compositions and methods are unique because they dramatically improve the quality and durability of chemically treated hair. Damage during chemical treatment is repaired, minimized, and/or compensated for due to a unique combination of components in the compositions that restructure, strengthen, or protect the keratin fibers of the hair. Hair treated with the compositions is surprisingly strengthened and the hair's cosmetic properties (e.g., softness, smoothness, and discipline) are considerably improved.

The unique combination of components that function to restructure the hair can be combined in an individual restructuring composition and applied to the hair before, after, or during a chemical treatment; or the unique combination of components can be included within the composition that chemically treats the hair (e.g., in a composition that further includes one or more active agent for chemically treating hair).

The restructuring compositions of the instant disclosure include: (a) one or more amines selected from the group consisting of diamines, polyamines, alkylamines, alkanolamines, and mixtures thereof; (b) one or more unsaturated carboxylic acids of formula (I):

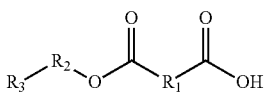

(I)

wherein $R_1$ is a linear or branched $C_2$-$C_{10}$ alkenyl group; $R_2$ is a linear or branched $C_1$-$C_{10}$ alkyl group; and $R_3$ is (meth)acryloyloxy.

The hair restructuring compositions are applied to the hair in methods for restructuring the hair. The restructuring compositions are applied to the hair and the one or more amines and the one or more unsaturated carboxylic acids may form a Michael adduct(s) in situ on hair. The formation of adducts is not necessarily instantaneous and therefore, when the one or more amines are mixed with the one or more unsaturated carboxylic acids immediately before application to the hair, most adducts are formed in situ on the hair after application. In some cases, the restructuring compositions can be applied to the hair within about 24 hours before or after chemically treating the hair. The hair restructuring compositions may also be applied to the hair simultaneously with a chemical treatment or added directly to a chemical treatment composition and applied as part of the chemical treatment composition to the hair. Non-limiting examples of chemical treatments include lightening, coloring, perming, and straightening of the hair. The methods do not require the use of heat. Accordingly, the methods may be carried out at room temperature (about 20° C. to about 30° C.) or at a temperature of about 10° C. to about 50° C.

As mentioned above, the hair structuring compositions can be added and mixed with a chemical treatment composition immediately before application to hair. In some cases, however, components of the hair structuring compositions can already be part of a composition for chemically treating hair, i.e., the unique components of the hair restructuring compositions ("restructuring components") can be formulated as part of a composition for chemically treating hair. This eliminates the step of separately applying a restructuring composition to the hair and/or eliminates the need for adding the restructuring composition to a chemical treatment composition before use. It also avoids the need for packing the restructuring composition separately from the chemical treatment composition.

The compositions for chemically treating hair typically include: (a) one or more amines selected from the group consisting of diamines, polyamines, alkylamines, alkanolamines, and mixtures thereof; (b) one or more unsaturated carboxylic acids of formula (I):

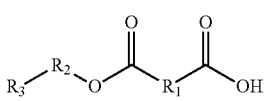

(I)

wherein $R_1$ is a linear or branched $C_2$-$C_{10}$ alkenyl group; $R_2$ is a linear or branched $C_1$-$C_{10}$ alkyl group; and $R_3$ is (meth)acryloyloxy. The one or more amines and the one or more unsaturated carboxylic acids may form a Michael adduct(s) in situ on hair. The formation of adducts is not necessarily instantaneous and therefore, when the one or more amines are mixed with the one or more unsaturated carboxylic acids immediately before application to the hair, most adducts are formed in situ on the hair after application.

The active agents are typically the compounds responsible, at least in part, for the chemically active nature of the compositions. Active agents include, for example, oxidizing agents, reducing agents, non-reducing agents for shaping hair, dyeing agents, and mixtures thereof. Accordingly, depending on the nature of the active agent(s), the composition for chemically treating the hair may be a hair lightening or bleaching composition, a hair coloring composition, a hair curling (perming) composition, a hair straightening composition, a hair relaxing composition, an anti-frizz composition, a hair smoothing composition, a hair conditioning composition, etc.

The compositions for chemically treating hair (the compositions already including the restructuring components) may be stand-alone compositions or may be used with or added to other compositions. For example, if the composition for chemically treating hair is a bleaching composition, it may be combined with a developer composition immediately before use. It is noted that either or both of the hair bleaching composition and the developer composition can include the hair restructuring components. Likewise, hair perming and hair straightening often requires more than one composition (e.g., relaxing compositions, activator compositions, neutralizer compositions, etc.). The restructuring components can be included in one or more (or all) of the various compositions.

The instant disclosure also relates to methods for chemically treating hair. For example, the compositions of the instant disclosure can be applied to the hair and allowed to remain on the hair for a period of time sufficient to achieve a desired result. Typically, a composition is allowed to remain on the hair for about 1 min. to about 45 min. and then the composition is rinsed from the hair. The methods do not require the use of heat, but can optionally be heated. Accordingly, the methods may be carried out at room temperature (about 20° C. to about 30° C.) or at a temperature of about 10° C. to about 50° C.; or at temperatures above about 30° C., 40° C., or 50° C.

The instant disclosure further relates to kits, which include one or more compositions described herein. For instance, in some cases, the kits include: (i) a restructuring composition as described above; (ii) a composition comprising one or more active agents for chemically treating hair; and (iii) optionally, a composition comprising one or more hair conditioning agents; wherein each of the compositions is maintained separately in the kit. The instant disclosure also relates to kits in instances where the restructuring components are already included in one or more compositions for chemically treating hair. For example, these kits may include: (i) a composition for chemically treating hair, as described above; (ii) a composition comprising one or more second active agents that may be different than the one or more active agents in (i); and (iii) optionally, a composition comprising one or more hair conditioning agents.

Finally, as referenced previously, the instant disclosure relates to methods of using the compositions to treat hair or to restructure hair. These methods include applying one or more compositions of the instant disclosure to the hair. The one more composition may be temporarily applied to the hair (e.g., applied for a period of about 1 hour or less), or may be allowed to remain on the hair for an indefinite amount of time. When the hair restructuring components are included with a composition for chemically treating the hair, the composition for chemically treating the hair is typically applied to the hair for an amount of time sufficient to carry out the desired chemical treatment (e.g., less than about 1 hour). The compositions for chemically treating the hair are then usually rinsed from the hair after the desired amount of chemical treatment has been achieved.

DETAILED DESCRIPTION OF THE DISCLOSURE

The instant disclosure relates to restructuring hair, in particular human hair of the head. In the context of the instant disclosure, the term "restructuring" relates to strengthening hair and minimizing and/or compensating for the damage caused to hair during chemical processing. Thus, a "restructuring composition" is a composition that strengthens hair by minimizing and/or compensating for the damage caused to the hair from environmental stress, cosmetic treatments (e.g., repeated washing, drying, heating, etc.), and from chemical processing. Restructured hair fibers (hair treated with the restructuring compositions) exhibit desirable cosmetic properties such as smoothness, gloss, improved combability, and improved strength and elasticity.

The unique combination of components that function to restructure the hair can be combined in an individual restructuring composition and applied to the hair before, after, or during a chemical treatment; or the unique combination of components can be included as part of the a composition that chemically treats the hair. In both situations, the one or more amines and the one or more unsaturated carboxylic acids may form a Michael adduct(s) in situ on hair. The formation of adducts is not necessarily instantaneous and therefore, when the one or more amines are mixed with the one or more unsaturated carboxylic acids immediately before application to the hair, most adducts are formed in situ on the hair.

Restructuring compositions according to the instant disclosure typically include:
(a) one or more amines selected from the group consisting of diamines, polyamines, alkylamines, alkanolamines, and mixtures thereof;
(b) one or more unsaturated carboxylic acids of formula (I):

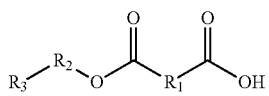

wherein $R_1$ is a linear or branched $C_2$-$C_{10}$ alkenyl group; $R_2$ is a linear or branched $C_1$-$C_{10}$ alkyl group; and $R_3$ is (meth)acryloyloxy; and
(c) a cosmetically acceptable carrier.

While not wishing to be bound by any particular theory, it is believed that the amine(s) interact with the unsaturated carboxylic acid(s) to form a Michael addition product, which is responsible, at least in part, for restructuring the hair and imparting the improved cosmetic properties to the hair, e.g., improved softness, smoothness, and discipline. A Michael reaction or Michael addition is the nucleophilic addition of a carbanion or another nucleophile to an α,β-unsaturated carbonyl compound. It is believed that Michael reactions occur and form Michael adduct(s) in situ on the hair, especially when the one or more amines are mixed with the one or more unsaturated carboxylic acids immediately before application to the hair. An adduct (a contraction of "addition product") is a product of a direct addition of two or more distinct molecules, resulting in a single reaction product containing all atoms of all components. Accordingly, a "Michael adduct" is an adduct formed by a Michael reaction.

The molar ratio of the (a) one or more amines to the (b) one or more unsaturated carboxylic acid is about 0.1:1 to about 1:0.1. In some cases, the molar ratio may about about 0.2:1 to about 1:0.2, about 0.3:1 to about 1:0.3, about 0.4:1 to about 1:0.4, about 0.5:1 to about 1:0.5, about 0.6:1 to about 1:0.6, about 0.7:1 to about 1:0.7, about 0.8:1 to about 1:0.8, about 0.9:1 to about 1:0.9, or about 1:1.

Various types of amines can be used in the compositions, including, for example, diamines, polyamines, alkylamines, alkanolamines. Appropriate amines are typical those capable of forming a Michael addition product with the one or more unsaturated carboxylic acids.

Non-limiting examples of diamines include 3,6-dioxa-1,8-octanediamine, 4,7,10-trioxa-1,13-tridecanediamine, 4,7-dioxa-1,10-decanediamine, 4,9-dioxa-1,12-dodecanediamine, dimethyl aminopropyl amine, 1,6-hexane diamine, 1,3 propane diamine, 2-methyl 1,5 pentane diamine, 1,3-pentanediamine, 1,3-diaminobutane, 1,2-bis(2-aminoethoxy)ethane, isophorone diamine, 1,3-bis(methylamine)-cyclohexane and mixtures thereof. In some cases, the compositions include at least 4,7,10-trioxa-1,13-tridecanediamine.

Non-limiting examples of polyamines include polyethyleneimine, a polyvinylamine, an aminated polysaccharide, an amine substituted polyalkylene glycol, an amine substituted polyacrylate crosspolymer, an amine substituted polyacrylate, an amine substituted polymethacrylate, an aminosilicone, a protein, an amine substituted polyester, a polyamino acid, an amodimethicone, a polyalkylamine, diethylene triamine, triethylenetetramine, spermidine, spermine, and mixtures thereof.

The one or more alkylamines and/or one or more alkanolamines that may be included in the compositions include compounds of formula (II):

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$ alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkylamines include methylamine, ethylamine, butylamine, octylamine, decylamine, dodecylamine, stearylamine, naphthylamine, benzylamine, aniline, cyclohexylamine, and mixtures thereof.

Non-limiting examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

The total amount of the one or more amines may vary, but in some cases, the total amount of the one or more amines is about 0.1 to about 50 wt. %, based on the total weight of the restructuring composition. In some cases, the total amount of the one or more amines is about 0.1 to about 50 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 3 to about 8 wt. %.

As mentioned previously, the compositions of the instant disclosure includes one or more unsaturated carboxylic acids of formula (I):

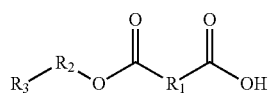
(I)

wherein $R_1$ is a linear or branched $C_2$-$C_{10}$ alkenyl group; $R_2$ is a linear or branched $C_1$-$C_{10}$ alkyl group; and $R_3$ is (meth)acryloyloxy. Non-limiting examples of unsaturated carboxylic acids of formula (I) include (meth)acryloyloxyethyl maleate, (meth)acryloyloxypropyl maleate, (meth)acryloyloxybutyl maleate, (meth)acryloyloxyethyl citraconate, (meth)acryloyloxypropyl citraconate, (meth)acryloyloxybutyl citraconate, (meth)acryloyloxyethyl dimethylmaleate, (meth)acryloyloxypropyl dimethylmaleate, (meth)acryloyloxybutyl dimethylmaleate, (meth)acryloyloxyethyl succinate, (meth)acryloyloxyethyl glutarate, (meth)allyloyloxyethyl maleate, and mixtures thereof. In some cases, the compositions include (meth)acryloyloxyethyl maleate (also referred to as "mono-2-(Methacryloyloxy)ethyl maleate" or "HEMA maleate").

The total amount of the one or more unsaturated carboxylic acids may vary but in some cases, the total amount is about 1 to about 50 wt. %, based on the total weight of the restructuring composition. In some cases, the total amount of the one or more mono-, di-, and/or tri-carboxylic acids is about 1 to about 40 wt. %, about 1 to about 30 wt. %, about 1 to about 25 wt. %, about 1 to about 20 wt. %, about 5 to about 50 wt. %, about 5 to about 40 wt. %, about 5 to about 30 wt. %, about 5 to about 25 wt. %, or about 5 to about 20 wt. %.

The compositions include a cosmetically acceptable carrier. The phrase "cosmetically acceptable" means that the item in question is compatible with keratinous substrates. For example, "cosmetically acceptable carrier" means a carrier that is compatible with a keratinous substrate and acceptable for application to the body, especially the body of a human.

The cosmetically acceptable carrier may include, for example, water and/or water soluble solvents. Non-limiting examples of cosmetically acceptable carriers include glycerin, $C_{1-4}$ alcohols, organic solvents, fatty alcohols, fatty ethers, fatty esters, polyols, glycols, vegetable oils, mineral oils, liposomes, laminar lipid materials, water, or any combinations thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Further to the above, in some cases, the restructuring compositions may include: (a) about 1 to about 25 wt. % of one or more amines selected from the group consisting of diamines, polyamines, alkylamines, alkanolamines, and mixtures thereof (preferably one or more alkanolamine and/or one or more diamines; and more preferably, monoethanolamine and/or 4,7,10-trioxa-1,13-tridecanediamine); (b) about 1 to about 50 wt. % of (meth)acryloyloxyethyl maleate; and (c) about 30 to about 90 wt. % of cosmetically acceptable carrier; wherein the molar ratio of (a):(b) is about 0.4:1 to about 1:0.4, preferably about 0.5:1 to about 1:0.5, most preferably, about 0.7:1 to about 1:0.7.

The components of the hair structuring compositions may already be part of a composition for chemically treating hair. The unique components of the hair restructuring compositions are formulated as part of a composition for chemically treating hair. Thus, the instant disclosure relates to compositions for chemically treating hair that typically include:
 (a) one or more amines selected from the group consisting of diamines, polyamines, alkylamines, alkanolamines, and mixtures thereof;
 (b) one or more unsaturated carboxylic acids of formula (I):

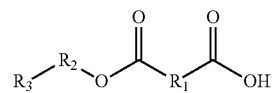
(I)

wherein $R_1$ is a linear or branched $C_2$-$C_{10}$ alkenyl group; $R_2$ is a linear or branched $C_1$-$C_{10}$ alkyl group; and $R_3$ is (meth)acryloyloxy; and
 (c) one or more active agents.

An "active agent," in the context of the instant disclosure, relates to a compound, molecule, or combination of compounds/molecules that chemically changes hair. For example, an active agent may reduce disulfide bonds, reestablish or form disulfide bonds, remove melanin from the hair, covalently bond to the hair, etc. Non-limiting examples of active agents include oxidizing agents, reducing agents, non-reducing agents for shaping hair, dyeing agents, and mixtures thereof. Based on the type of active agent, the composition for chemically treating hair may be a hair lightening or bleaching composition, hair coloring composition, a hair perming or straightening composition, a hair relaxing composition, an anti-frizz composition, a hair smoothing composition, a hair conditioning composition, or a mixture thereof.

Hair lightening compositions typically include one or more oxidizing agents. Non-limiting examples of oxidizing agents include peroxides, persulfates, perborates, percarbonates, and mixtures thereof. In some cases, the hair lightening composition includes one or more persulfates, such as those selected from the group consisting of sodium persulfate, potassium persulfate, ammonium persulfate, and mixtures thereof. In some cases, the hair lightening compositions include peroxide, such as hydrogen peroxide.

Hair perming or straightening compositions typically include one or more reducing agents. Non-limiting examples of reducing agents include cysteine or a derivative of cysteine, cysteamine or a derivative of cysteamine, thiolactic acid or an ester of thiolactic acid, thioglycolic acid or an ester of thioglycolic acid, thioglycerol, and mixtures thereof. In some cases, the reducing agent is a glyceryl or glycol monothioglycolate, diammonium dithiodiglycolate, ammonium thioglycolate, or a mixture thereof.

Hair straightening or relaxing compositions may include one or more non-reducing agents for shaping hair. Non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

The non-hydroxide compounds may include one or more ethyleneamines, alkanolamines, amino acids, or mixtures thereof. Non-limiting examples of non-hydroxide compounds include ethylenediamine, monoethanolamine, diethanolamine, propanolamine, isopropanolamine, triethanolamine, butanolamine, isobutanolamine, methylethanolamine, butylethanolamine, arginine, lysine, and mixtures thereof.

In some cases, when the compositions include hydrogen peroxide as an active agent, the composition further comprises a second oxidizing agent other than hydrogen peroxide and/or the compositions includes an oxidative dye precursor. For example, in some cases the second oxidizing agent is a persulfate. Non-limiting examples of persulfates include potassium persulfate, sodium persulfate, ammonium persulfate, and mixtures thereof.

Hair coloring or dyeing compositions typically include one or more colorants or dyeing agents. Non-limiting examples of colorants or dyeing agents include direct dyes, oxidative dyes, direct action dyes, natural dyes, metallic dyes, reactive dyes, and mixtures thereof.

The compositions for chemically treating hair can include varying amounts of components depending on the purpose of the composition and depending on whether the composition will be combined with additional compositions. Typically, when the restructuring components are already included in a composition with the one or more active agents, the total amount of each of the restructuring agents will be less than for a restructuring composition that includes primarily the restructuring agents. The total amount of each of the restructuring components will be reduced relative to the total weight of the composition due to the addition of the one or more active agents and the additional components included in the composition for chemically treating hair.

With respect to the total amount of the one or more amines, the composition for chemically treating hair may include about 0.01 to about 25 wt. %, about 0.01 to about 20 wt. %, 0.01 to about 15 wt. %, about 0.01 to about 10 wt. %, about 0.01 to about 5 wt. %, about 0.01 to about 4 wt. %, about 0.01 to about 3 wt. %, about 0.1 to about 20 wt. %, about 0.01 to about 15 wt. %, about 0.1 to about 10 wt. %, about 0.1 to about 5 wt. %, about 0.1 to about 4 wt. %, about 0.1 to about 3 wt. %, about 0.5 to about 4 wt. %, about 0.5 to about 3 wt. %, or about 1 to about 3 wt. %.

With respect to the total amount of the one or more unsaturated carboxylic acids, the compositions for chemically treating hair may include about 0.01 to about 25 wt. %, about 0.01 to about 20 wt. %, about 0.01 to about 15 wt. %, 0.01 to about 10 wt. %, about 0.01 to about 8 wt. %, about 0.01 to about 4 wt. %, 0.01 to about 3 wt. %, about 0.01 to about 2 wt. %, about 0.05 to about 20 wt. %, about 0.05 to about 15 wt. %, about 0.05 to about 10 wt. %, about 0.05 to about 8 wt. %, about 0.05 to about 4 wt. %, about 0.05 to about 3 wt. %, 0.1 to about 15 wt. %, 0.01 to about 10 wt. %, 0.1 to about 5 wt %, about 0.01 to about 2 wt. %, or about 0.1 to about 2 wt. %.

With respect to the total amount of the one or more active agents, the composition may include about 0.01 to about 85 wt. %, about 0.01 to about 50 wt. %, about 0.01 to about 25 wt. %, about 0.01 to about 20 wt. %, about 0.01 to about 10 wt. %, about 0.01 to about 5 wt. %, about 1 to about 85 wt. %, about 1 to about 70 wt. %, about 1 to about 60 wt. %, about 1 to about 50 wt. %, about 1 to about 25 wt. %, or about 1 to about 10 wt. %, about 25 to about 95 wt. %, about 40 wt. % to about 95 wt. %, or about 50 wt. % to about 80 wt. %.

The instant disclosure further relates to methods for treating and/or restructuring hair using the restructuring compositions and the compositions for chemically treating hair. For instance, the instant disclosure relates to methods for restructuring hair, the methods comprising applying a hair restructuring composition to the hair. The hair restructuring composition may be temporarily applied to the hair for a sufficient amount of time to restructure the hair and then removed, for example, by rinsing. Alternatively, the restructuring composition may be a "leave-in" composition that does not require removal from the hair.

The methods are unique because they do not require heat to attain the dramatic improvements in cosmetic and/or sensorial properties (e.g., softness, smoothness, discipline, conditioning, etc.). Thus, the methods are typically carried out at room temperature (about 20° C. to about 30° C.). In particular, methods can be performed without allowing the hair and the compositions applied to the hair to reach a temperate above about 50° C. or about 60° C. The methods can be performed without applying heat during treatment or after treatment. Accordingly, the methods may be carried out at a temperature of about 10° C. to about 60° C., about 15° C. to about 50° C., about 15° C. to about 40° C., or about 15° C. to about 30° C. However, heat can optionally be applied with the methods. For example, the compositions for chemically treating hair can be applied to the hair and then heated, for example, to a temperature above about 40° C., 50° C., 60° C., 70° C., 80° C., 100° C., 120° C., 150° C. or higher.

The restructuring composition may be applied to the hair within about 1 hour, about 45 min., about 30 min., about 20 min., about 15 min., about 10 min., or about 5 min. of chemically treating the hair (before or after the chemical treatment). For example, the restructuring composition may be applied to the hair followed by application of a chemical treatment composition. Alternatively, a chemical treatment composition may be applied to the hair followed by application of a restructuring composition. In some cases, a restructuring composition is applied both before and after a chemical treatment composition is applied to the hair. In some cases, when applying a restructuring composition to the hair after chemical treatment, the chemical treatment composition is first rinsed from the hair before application of the restructuring composition. The hair restructuring composition can be applied to the hair and allowed to dry on the hair, naturally or with the use of heat and/or air (blow dry). Without rinsing the restructuring composition from the hair, a chemical treatment composition can subsequently be applied to the hair. In some cases, a restructuring composition is applied to the hair within about 1 hour, about 45 min., about 30 min., about 20 min., about 15 min., about 10 min., or about 5 min. before application of a chemical treatment composition. Likewise, in some cases, a restructuring composition is applied to the hair within about 1 hour, about 45 min., about 30 min., about 20 min., about 15 min., about 10 min., or about 5 min. after application of a chemical treatment composition. In some cases, the restructuring composition is applied simultaneously with a hair treatment composition or is added directly to the hair treatment composition before application to the hair.

If the hair treatment composition is for lightening hair, a method for lightening hair can include: (i) mixing a hair restructuring composition with a bleaching composition, and optionally with a composition comprising one or more hair conditioning agents and/or one or more direct dyes; (ii) applying the mixture onto hair and allowing the mixture to remain on the hair for about 1 to about 45 minutes; and (iii) rinsing the mixture from hair. If the hair treatment composition is for perming or straightening the hair, a method for perming and/or straightening the hair may include: (i) mixing a restructuring composition with a reducing compositions and/or with a neutralizing composition; and (ii) applying the reducing composition and/or the neutralizing composition to the hair for about 1 to about 45 minutes. Usually, the reducing composition and the neutralizing composition are applied sequentially.

The instant disclosure also relates to methods for chemically treating hair using chemical compositions already formulated to include the restructuring agents of the restructuring compositions. Typically, the compositions for chemically treating hair are applied to the hair for a sufficient amount of time to attain a desired result, and then rinsed from the hair. The compositions for chemically treating hair may be applied to the hair for about 1 hour, about 45 min, about 30 min, about 20 min, about 15 min, about 10 min, or about 5 min., and then rinsed from the hair. For example, if the composition for chemically treating hair is a hair lightening composition, a method for lightening the hair may include: (i) mixing a hair lightening composition with a developer composition comprising a peroxide, and optionally with a composition comprising one or more hair conditioning agents and/or one or more direct dyes; (ii) applying the mixture onto hair and allowing the mixture to remain on the hair for about 1 to about 45 minutes; and (iii) rinsing the mixture from hair. In some cases, however, the restructuring components may be formulated with the developer composition comprising a peroxide, such that the developer composition instead of with the hair lightening composition. In some cases, the restructuring components may be included in both the hair lightening composition and the developer composition.

The compositions described in the instant disclosure may be included in kits for treating hair. Kits typically include more than one composition and therefore more than one container (or more than one compartment in a given container) to ensure that various compositions do not come into contact with each other until desired. For example, the kits may include a restructuring composition, as described previously, or may include a composition for chemically treating hair (compositions already formulated to include the restructuring agents of the restructuring compositions). The kits may further include a developer bottle, gloves, shampoo, conditioner, and/or an odor eliminator. Instructions for use of the kit are also typically provided.

In some cases, the kits include: (i) a restructuring composition; (ii) a composition comprising one or more active agents for chemically treating hair; and (iii) optionally, a composition comprising one or more hair conditioning agents. In some cases, the kit further includes a second composition comprising one or more active agents (typically active agents that are different than in the composition of (ii)). For example, the composition of (ii) may include, as an active agent, one or more oxidizing agents selected from the group consisting of persulfates, perborates percarbonates, alkali metal bromates, ferricyanides, peroxygenated salts, and mixtures thereof. The second composition may be, for example, a developer composition that includes peroxide. Likewise, the composition of (ii) may include, as an active agent, one or more reducing agents for perming or straightening the hair and the second composition may be a neutralizing composition wherein the one or more active agents are reducing agents.

In instances where the restructuring components of the restructuring compositions are already formulated into a composition for chemically treating hair, the kits will typically include: (i) a composition for chemically treating hair; and (ii) optionally, a composition comprising one or more hair conditioning agents. Such kits may also include a composition comprising one or more second active agents (typically different than the active agents already in (i)). For example, if the composition for chemically treating hair is a hair lightening composition, the kit may include a developer composition. The restructuring agents may be included in either the hair lightening composition or the developer composition, or both. If the composition is for perming or straightening hair, the restructuring agents may be included in the reducing composition or in the neutralizing composition, or both.

Preservatives, conditioning agents including cationic conditioning agents, colorants or dyes, thickeners, surfactants including ionic surfactants, nonionic surfactants, amphoteric surfactants and/or zwitterionic surfactants, stabilizers, pH modifiers, buffers, etc., may also optionally be included (or excluded) from the compositions.

The instant disclosure additionally relates to methods for making the restructuring compositions and the chemical treatment compositions (the composition for chemically treating hair). For instance, methods for making the restructuring compositions of the disclosure include: (a) combining the one or more amines selected from the group consisting of diamines, polyamines, alkylamines, alkanolamines, and mixtures thereof with (b) one or more unsaturated carboxylic acids of formula (I) in a (c) solvent; and forming a Michael addition product from (a) and (b).

Typically, the solvent is an organic solvent. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, the solvent may comprise water, a mixture of water and at least one organic solvent, or at least one cosmetically acceptable organic solvent. Additionally, cosmetically acceptable solvents may be or may include ethanol, a glycol ether, for example, dipropylene glycol n-butyl ether, isododecane, mineral oil, propylene glycol, pentylene glycol, hexylene glycol, glycerol, and mixtures thereof.

Methods of making the compositions for chemically treating hair include: making or obtaining a restructuring compositions as discussed above; and combining the restructuring compositions with one or more active agents.

More exhaustive but non-limiting lists of components that are useful in the compositions of the instant disclosure are presented below.

Amines

Alkylamines and Alkanolamines

The one or more alkylamines and/or one or more alkanolamines that may be included in the compositions include compounds of formula (II):

$$NR_3R_4R_5 \quad (II)$$

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$ alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkanolamines include monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

$$RN(R')_2$$

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

In some cases, alkylamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Amidoamines

Other non-limiting examples of alkyl monoamines include amidoamine compounds corresponding to the following formula and their salts:

$$RCONHR'N(R'')_2$$

wherein: R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

Monoamines

Non-limiting examples of specific monoamines include methylamine, ethylamine, isopropylamine and n-propylamine, or of a diamine selected from the group consisting of ethylenediamine, 1,2-propanediamine, 1,3-propanediamine, 1,2-butanediamine, 1,3-butanediamine and 1,4-butanediamine or of an alkanolamine selected from the group consisting of monoethanolamine, 2-aminopropan-1-ol and 1-aminopropan-2-ol, or of a specialty amine selected from the group consisting of 1,2,3-triaminopropane, 1,3-diaminopropan-2-ol, 1,2-diamino-propan-3-ol, 1-aminopropanediol, 2-aminopropanediol, glucosamine and isomaltine and/or piperazine, or of a piperazine derivative selected from the group consisting of 2-methylpiperazine, 2,6-dimethylpiperazine, 2,5-dimethylpiperazine, 2,5-bis(aminomethyl)piperazine, 2,6-bis(aminomethyl)piperazine, 2-aminomethyl-5-methylpiperazine and 2-aminomethyl-6-methylpiperazine The monoamine may be an alkoxylated monoamine. The alkoxylated monoamines are chosen from amine compounds having an amino group and at least one degree of alkoxylation. The alkoxylation is provided by an alkylene oxide group which is often chosen from ethylene oxide and propylene oxide.

Non-limiting examples of suitable alkoxylated monoamines that may be used in the compositions of the instant disclosure include compounds corresponding to the following formula:

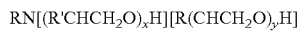
RN[(R'CHCH$_2$O)$_x$H][R(CHCH$_2$O)$_y$H]

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 provided that the sum of x+y is >0; the groups R', which may be identical or different, represent hydrogen, or an alkyl group such as a methyl group. Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Non-limiting examples of alkoxylated monoamines include PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding the following formula:

RNR"[(R'CHCH$_2$O)$_x$H]

wherein R is a hydrocarbon radical containing at least 6 carbon atoms. R can be linear or branched, acyclic or cyclic, saturated or unsaturated, aliphatic or aromatic, substituted or unsubstituted; x represents a number of from 1 to 100; R' represents hydrogen, or an alkyl group such as in particular a methyl group; and R" is a hydrogen or a hydrocarbon radical. Typically, R is a linear or branched, acyclic alkyl or alkenyl group or an alkyl phenyl group; x is typically a number from 1 to 30. When R" is a hydrocarbon radical group, this group may be linear or branched, saturated or unsaturated, substituted or unsubstituted. The hydrocarbon radical represented by R" may also contain an alkoxylated moiety (as defined by [(R'CHCH$_2$O)$_y$H]), and/or heteroatoms such as nitrogen. When R" contains at least one alkoxylated moiety, the total number of alkoxylation in the formula may range from 1 to 120. Examples of alkoxylated monoamines include PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to the following formula:

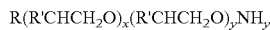
R(R'CHCH$_2$O)$_x$(R'CHCH$_2$O)$_y$NH$_y$.

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 with the proviso that the sum of x+y is >0; the groups R', which may be identical or different, represent hydrogen, or an alkyl group such as in particular a methyl group. Typically, R is a linear or branched, acyclic alkyl or alkenyl group or an alkyl phenyl group; x and y, independently of one another, are each typically a number from 0 to 30. Examples of alkoxylated monoamines include polyetheramines containing a monoamine group. These polyetheramines are commercially available from Hunstman under the tradename JEFFAMINE (M series such as M-600, M-1000, M-2005 and M-2070) and SURFONAMINE series (B-60, B-100, B-200, L-100, L-200, L-207, L-300).

In some cases, the monamines may be selected from the group consisting of 3-isopropoxypropylamine, 3-methoxypropylamine, tris(hydroxymethyl)aminomethane, 3-ethoxypropylamine, 3-(2-ethylhexyloxy)-propylamine, 2-(2-aminoethoxy)ethanol, 3-butoxypropylamine, and monoethanolamine, and mixtures thereof.

Diamines

Non-limiting examples of diamines that may be useful may be primary amines and secondary amines. The diamine can include both primary and secondary amine groups. Optional diamines may include at least one ethylene oxide group. For example, between 1 and 4 ethylene oxide groups can be present in the diamine. The diamine may optionally include propylene oxide groups. For example, between 1 and 4 propylene oxide groups can be present in the diamine. Non-limiting examples of diamines include 4, 9-dioxadodecane-diamine; 4, 7, 10-trioxa-1,13-tridecanediamine; ethylenediamino; polyoxypropylene diamine; polyethylene glycol diamine; triethylene glycol diamine (2OE); n-(2-hydroxyethyl)-ethylenediamine; 1,3-diaminopropane; 1,7-diaminoheptane; 1,4-diaminobutane; 1,2-diaminopropane; 1,6-diaminohexane; 1, 11-diamino-3,6,9-trioxaundecane; 1,5-diaminopentane; polyoxyethylene diamine; 2,2-dimethyl-1, 3-propanediamine; 2,2-bis(aminoethoxy)propane; 4,7, 10-trioxa-1, 13-tridecanediamine; 1,3-diaminopentane; 4,7, 10-trioxa-1, 13; 1, 5-diamino-2-methylpentane; (3s,4s)-(−)-3,4-hexanediamine dihydrochloride; 1,9-diaminonane, and mixtures thereof.

In some cases, diamines may be selected from the group consisting of 4,9-dioxadodecane-diamine, 4, 7, 10-trioxa-1, 13-tridecanediamine, ethylenediamino, polyoxypropylene diamine, polyethylene glycol diamine, triethylene glycol diamine (2OE); n-(2-hydroxyethyl)-ethylenediamine; 1,3-diaminopropane, 1,7-diaminoheptane, 1,4-diaminobutane, 1,2-diaminopropane, 1,6-diaminohexane, 1,11-diamino-3,6, 9-trioxaundecane, 1,5-diaminopentane, polyoxyethylene diamine, 2,2-dimethyl-1,3-propanediamine, 2,2-bis(aminoethoxy)propane, 4,7,10-trioxa-1,13-tridecanediamine, 1,3-diaminopentane, 4,7,10-trioxa-1,13; 1,5-diamino-2-methylpentane, (3s,4s)-(−)-3,4-hexanediamine dihydrochloride, 1,9-diaminononane, and mixtures thereof.

Polyamines

Polyamines have more than two amino groups. In some cases, the composition of the instant disclosure may include one or more polyamines, but in some cases, the compositions are free or essentially free of polyamines. The polyamine may be, for example, aminated polysaccharides comprising multiple amino groups, such as, for example, hydrolysates of aminated polysaccharides.

The polyamine may also be a polymer comprising multiple amino groups including homopolymers, copolymers, and terpolymers.

In some cases, polyamines are chosen from polyethyleneimines. Polyethyleneimines may optionally be substituted. Non-limiting examples of polyethyleneimines which may be used include LUPASOL products commercially available from BASF. Suitable examples of LUPASOL polyethyleneimines include LUPASOL PS, LUPASOL PL, LUPASOL PR8515, LUPASOL G20, LUPASOL G35 as well as LUPASOL SC Polythyleneimine Reaction Products (such as LUPASOL SC-61B, LUPASOL SC-62J, and LUPASOL SC-86X). Other non-limiting examples of polyethyleneimines which may be used in the composition according to the present invention are the EPOMIN products commercially available from Aceto. Suitable examples of EPOMIN polyethyleneimines include EPOMIN SP-006, EPOMIN SP-012, EPOMIN SP-018, and EPOMIN P-1000. Suitable polyamines s also be chosen from polyvinylamines. Examples thereof include LUPAMINES 9095, 9030, 9010, 5095, 1595 from BASF.

The polyamine compounds can also be substituted. An example of such a compound is PEG-15 Cocopolyamine from Cognis.

In some cases, the polyamine is chosen from proteins and protein derivatives. Non-limiting examples of suitable proteins and protein derivatives f include those listed at pages 1701 to 1703 of the C.T.F.A. International Cosmetic Ingredient Dictionary and Handbook, 8$^{th}$ edition, vol. 2, (2000), which is incorporated herein by reference in its entirety. In some cases, the at least one polyamine is chosen from wheat protein, soy protein, oat protein, collagen, and keratin protein.

The polyamine may be an alkoxylated polyamine. The alkoxylated polyamines may be chosen from amine compounds having at least two amino groups and at least one degree of alkoxylation. The alkoxylation is provided by an alkylene oxide group which may be chosen from ethylene oxide and propylene oxide. Non-limiting examples of suitable alkoxylated polyamines include compounds corresponding to the following formula:

$$NH_2R(R'CHCH_2O)_x(R'CHCH_2O)_y(R'CHCH_2O)_z—RNH_2$$

wherein R represents a —CH2-, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted; x, y, and z independently of one another, represent numbers of from 0 to about 100; R' represents hydrogen, or an alkyl group, preferably a methyl group; and The sum of x+y+z is at least 1. In some cases, R is a linear or branched, acyclic alkyl or alkenyl group or an alkyl phenyl group; x, y, and z independently of one another, preferably represent numbers ranging from 2 to 100.

Non-limiting examples of the alkoxylated polyamines include, for example, tetradecyloxypropyl-1,3-diaminopropane; a C$_{12-14}$ alkyl oxypropyl-1,3-diaminopropane; a C$_{12-15}$ alkyloxypropyl amine and other similar materials that are commercially available from Tomah under the tradename of TOMAH DA-17. Other examples of alkoxylated polyamines are diamine compounds belonging to the Jeffamine series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting examples of suitable alkoxylated polyamines in the diamine form include compounds corresponding to the following formula:

$$NH_2(CH_2)_xOCH_2CH_2O(CH_2)_xNH_2$$

wherein x is 2 or 3.

Examples of alkoxylated polyamines are diamine compounds belonging to the JEFFAMINE series available from Huntsman Corporation, Salt Lake City, Utah, such as JEFFAMINE EDR148, and JEFFAMINE EDR176.

Additional non-limiting examples of alkoxylated polyamines in the triamine form include compounds corresponding to the following formula:

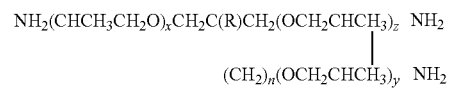

wherein R is hydrogen, —CH$_2$ or —C$_2$H$_5$, n=0 or 1, and x, y, and z independently of one another, represent numbers of from 0 to 100 and the sum of x+y+z is at least 1.

Examples of alkoxylated polyamines are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

The total amount of the one or more amines may vary depending on the type of composition. In some cases, the total amount of the one or more amines is about 0.1 to about 35 wt. %, based on the total weight of the composition. In some cases, the total amount of the one or more amines is about 0.1 to about 30 wt. %, about 0.1 to about 25 wt. %, about 0.1 to about 20 wt. %, about 0.1 to about 15 wt. %, about 0.1 to about 10 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 1 to about 35 wt. %, about 1 to about 30 wt. %, about 1 to about 25 wt. %, about 1 to about 20 wt. %, about 1 to about 15 wt. %, about 1 to about 10 wt. %, or about 3 to about 8 wt. %.

Cosmetically Acceptable Carrier

The cosmetically acceptable carrier can include, for example, glycerin, C$_{1-4}$ alcohols, organic solvents, fatty alcohols, fatty ethers, fatty esters, polyols, glycols, vegetable oils, mineral oils, liposomes, laminar lipid materials, water, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some cases, the restructuring compositions and/or the compositions for chemically treating hair may include about 50 to about 96 wt. % of a cosmetically acceptable carrier, based on the total weight of the composition. Further, the total amount of the cosmetically acceptable carrier may be 50 to 95 wt. %, 50 to 92 wt. %, 50 to 90 wt. %, 50 to 85 wt. %, 50 to 80 wt. %, 55 to 95 wt. %, 55 to 92 wt. %, 55 to 90 wt. %, 55 to 85 wt. %, 55 to 80 wt. %, 60 to 95 wt. %, 60 to 92 wt. %, 60 to 90 wt. %, 60 to 85 wt. %, or 60 to 80 wt. %.

In some cases, the cosmetically acceptable carrier includes one or more glycols. For example, the one or more glycols can include ethylene glycol, propylene glycol, butylene glycol, caprylyl glycol, hexylene glycol, dipropylene glycol, and diethylene glycol. The total amount of the one or more glycols, if present, may be 5 to 40 wt. %, 5 to 35 wt. %, 5 to 30 wt. %, 5 to 25 wt. %, 5 to 20 wt. %, 10 to 40 wt. %, 10 to 35 wt. %, 10 to 30 wt. %, 10 to 25 wt. %, 10 to 20 wt. %, 15 to 40 wt. %, 15 to 35 wt. %, 15 to 30 wt. %, 15 to 25 wt. %, 15 to 20 wt. %, 20 to 40 wt. %, 20 to 35 wt. %, or 20 to 30 wt. %, based on the total weight of the composition.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Active Agents

Oxidizing Agents

Oxidizing agents may be selected from, for example, peroxides, persulfates, perborates percarbonates, alkali metal bromates, ferricyanides, peroxygenated salts, or a mixture thereof. Oxidizing agents that may also be used include at least one redox enzyme such as laccases, peroxidases, and 2-electron oxidoreductases, such as uricase, where appropriate in the presence of their respective donor or co-factor. Oxygen in the air may also be employed as an oxidizing agent.

In some cases, the oxidizing agent is a persulfate and/or a monopersulfate such as, for example, potassium persulfate, sodium persulfate, ammonium persulfate, as well as mixtures thereof. In one embodiment, the oxidizing agents in the present disclosure are selected from hydrogen peroxide, potassium persulfate, sodium persulfate, and mixtures thereof.

One or more oxidizing agents are typically included in an oxidizing composition. An oxidizing composition may be a hair lightening or bleaching composition or it may be a neutralizing composition or a developer composition. In some cases, the total amount of the one or more oxidizing agents in an oxidizing composition is essentially 100% (as is the case for some powdered oxidation compositions). In some cases, the total amount of the one or more oxidizing agents is about 1 to about 80 wt. %, about 1 to about 70 wt. %, about 1 to about 60 wt. %, about 1 to about 50 wt. %, about 1 to about 40 wt. %, about 5 to about 80 wt. %, about 5 to about 70 wt. %, about 5 to about 60 wt. %, about 5 to about 50 wt. %, about 5 to about 40 wt. %, about 10 to about 80 wt. %, about 10 to about 70 wt. %, about 10 to about 60 wt. %, about 10 to about 50 wt. %, or about 10 to about 40 wt. %, based on the total weight of the composition.

Reducing Agents

Reducing agents are well known for use in hair care compositions. Typical reducing agents are capable of reducing the disulfide bonds in the hair to produce free thiol groups. Non-limiting examples of suitable reducing agents include thioglycolic acid and thioglycolic acid salts and esters, thiolactic acid and thiolactic acid salts and esters, cysteine thioglycerol, thioglycolic hydrazide, thioglycolamide, glycerol monothioglycolate, sodium metabisulfite, beta-mercaptopropionic acid, N-hydroxyethyl mercapto-acetamide, N-methyl mercapto-acetamide, beta-mercapto-ethylamine, beta-mercaptopropionamide, 2-mercapto-ethanesulfonic acid, dimercaptoadipic acid, dithiothreitol, homocysteinethiolactone, cysteine derivatives, polythiol derivatives formed by the addition of cysteamine onto a maleic anhydride-alkylvinylether copolymer, inorganic sulfites, inorganic bisulfites, cysteamine and its derivatives, dithioerythritol, organic phosphines, and mixtures thereof.

One or more reducing agents may be included in reducing compositions. The total amount of the one or more reducing agents can vary, but in some cases, the total amount of the one or more reducing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Neutralizing Agents

Neutralizing agents are well known for use in hair care compositions. In some cases, after treating hair with compositions of the present disclosure comprising active agents chosen from reducing agents for curling or shaping the hair (as in perming and hair straightening systems), the hair is treated with a neutralizing agent or composition containing a neutralizing agent. For instance, the neutralizing agent may be an oxidizing agent chosen from hydrogen peroxide, urea hydrogen peroxide, alkali metal bromates, or persalts, such as perborates and persulphates. One or more neutralizing agents may be included in neutralizing compositions. The total amount of the one or more neutralizing agents can vary, but in some cases, the total amount of the one or more neutralizing agents is about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Non-Reducing Agents for Shaping Hair

Non-reducing agents for shaping hair may be one or more hydroxide compounds, non-hydroxide compounds, or mixtures thereof. For instance, the hydroxide compounds may be alkali metal hydroxides, alkaline-earth metal hydroxides, transition metal hydroxides, and mixtures thereof. Non-limiting examples include of hydroxide compounds include sodium hydroxide, potassium hydroxide, lithium hydroxide, calcium hydroxide, magnesium hydroxide, barium hydroxide, strontium hydroxide, manganese hydroxide, zinc hydroxide, guanidine hydroxide, and mixtures thereof.

Colorants

Hair color-altering compositions may comprise or may be formed from one or more of hair lightening compositions, hair bleaching, colorants, or hair coloring compositions. Before, after, or simultaneously with the hair lightening composition, a color-altering composition may be used. For example, the hair color-altering composition may be formed by combining a hair lightening composition according to the instant disclosure, a developer composition (typically comprising hydrogen peroxide) and a colorant. In other examples, the color-altering composition may be formed by combining a hair coloring composition containing at least one colorant and a developer composition. Typically, the least one colorant compound is chosen from oxidative dye precursors, direct dyes, pigments, and mixtures thereof. The oxidation dyes are generally chosen from one or more oxidation bases optionally combined with one or more couplers. By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(3-hydroxyethyl)-para-phenylenediamine, 4-N,N-bis(3-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N-bis(4'-aminophenyl)-1,3-diaminopropano-I, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamin-e, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds such as 2,5-diaminopyridine, 2-(4-methoxyphenyl)amino-3-aminopyridine and 3,4-diaminopyridine, and the addition salts thereof. Other pyridine oxidation bases that are useful in the present disclosure are the 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-.quadrature.-hydroxyethoxy-3-amino-pyrazolo[1,5-a]pyridine; 2-(4-dimethylpyperazinium-1-yl)-3-amino-pyrazolo[1,5-a]pyridine; and the addition salts thereof.

More particularly oxidation bases that are useful in the present disclosure are selected from 3-aminopyrazolo-[1,5-a]-pyridines and preferably substituted on carbon atom 2 by:

(a) one (di)($C_1$-$C_6$)(alkyl)amino group wherein said alkyl group can be substituted by at least one hydroxy, amino, imidazolium group;

(b) one heterocycloalkyl group containing from 5 to 7 members chain, and from 1 to 3 heteroatoms, potentially cationic, potentially substituted by one or more ($C_1$-$C_6$-alkyl, such as di(C1-C4)alkylpiperazinium; or (c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(β-hydroxyethyl)pyrazole, 3,4-diamino-pyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4, 5-diamino-1-ethyl-3-methyl-pyrazole, 4, 5-diamino-1-ethyl-3-(4'-methoxyphenyl)pyrazole, 4, 5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-on-e, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-o-ne. 2,3-Diamino-6,7-dihydro-1H,5H-pyrazolo[1,2-a]pyrazol-1-one and/or a salt thereof will preferably be used. 4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Composition according to the present disclosure may optionally comprise one or more couplers advantageously chosen from those conventionally used in the dyeing or coloring of keratin fibers.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diamino-phenoxy)propane, 3-ureidoaniline, 3-ureido-1-dimethylamino-benzene, sesamol, 1-β-hydroxyethylamino-3,4-methylene-dioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylene-dioxybenzene, 2,6-bis(J-hydroxyethylamino)toluene, 6-hydroxy-indoline, 2,6-dihydroxy-4-methylpyridine, 1-H-3-methylpyrazol-5-one, 1-phenyl-3-methylpyrazol-5-one, 2,6-dimethyl-pyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure are especially selected from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the compositions of the present disclosure.

The coupler(s), if they are present, each advantageously represent from 0.001% to 10% by weight relative to the total weight of the composition, and preferably from 0.005% to 5% by weight relative to the total weight of the compositions of the present disclosure.

Compositions according to the disclosure may optionally comprise b) one or more synthetic or natural direct dyes, chosen from anionic and nonionic species, preferably cationic or nonionic species, either as sole dyes or in addition to the oxidation dye(s).

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Many direct dyes are cationic direct dyes. Mention may be made of the hydrazono cationic dyes of formulas (Va) and (V'a), the azo cationic dyes (Via) and (VI'a) and the diazo cationic dyes (Vila) below:

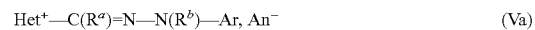  (Va)

Het⁺—C(Rᵃ)=N—N(Rᵇ)—Ar, An⁻

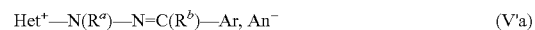  (V'a)

Het⁺—N(Rᵃ)—N=C(Rᵇ)—Ar, An⁻

  (Vla)

Het⁺—N=N—Ar, An⁻

  (VI'a) and

Ar⁺—N=N—Ar", An⁻

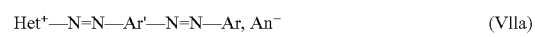  (Vlla)

Het⁺—N=N—Ar'—N=N—Ar, An⁻ in which formulas (Va), (V'a), (VIa), (VI'a) and (VIIa):

Het⁺ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar⁺ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy Ar" is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group;

An$^-$ represents an anionic counter-ion such as mesylate or halide. In particular, mention may be made of the azo and hydrazono cationic dyes bearing an endocyclic cationic charge of formulae (Va), (V'a) and (Via) as defined previously. More particularly those of formulae (Va), (V'a) and (Via) derived from the dyes described in patent applications WO 95/15144, WO 95/01772 and EP-714954, which are incorporated herein by reference in their entirety.

In some cases, the cationic part is derived from the following derivatives:

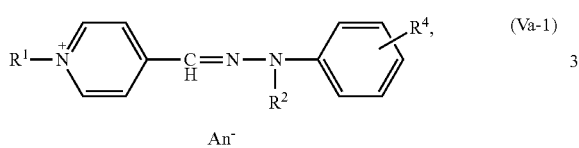

(Va-1)

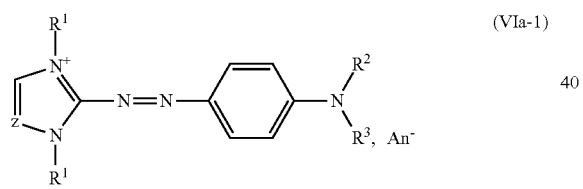

(VIa-1)

wherein in formulae (Va-1) and (Via-1):

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$)(alkyl)amino optionally substituted on the alkyl group(s) with a hydroxyl group; particularly, $R^4$ is a hydrogen atom, Z represents a CH group or a nitrogen atom, preferentially CH;

An$^-$ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

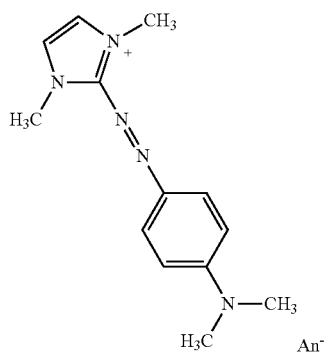

Basic Red 51

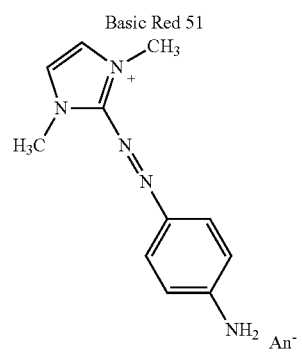

Basic Orange 31

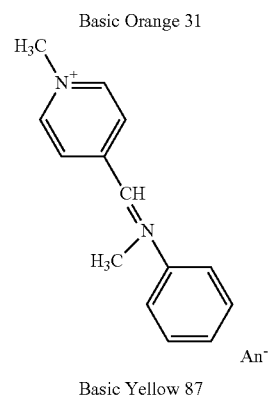

Basic Yellow 87

Among the natural direct dyes that may be used according to the disclosure, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

When they are present, the direct dye(s) more particularly represent from 0.001% to 10% by weight and preferably from 0.005% to 5% by weight of the total weight of the compositions of the present disclosure.

Additional Components

Cationic Conditioning Compounds

The cationic conditioning agent employed in the compositions of the present invention can be a monoalkyl quaternary amine, such as stearyltrimonium chloride, soyatrimonium chloride or coco-ethyldimonium ethosulfate. Other suitable cationic conditioning agents include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic conditioning agents may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic conditioning agents are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryoloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic conditioning agents are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 in the CTFA Cosmetic Ingredient Dictionary, 3rd Ed., published in 1982 by the Cosmetic Toiletry and Fragrance Association, Inc. (hereafter CTFA Dictionary and CTFA name), is sold under the trademark MERQUAT-100, and is described as having a weight average molecular weight of approximately 100,000. A copolymer reaction product of dimethyldiallylammonium chloride with acrylamide monomers is named Polyquaternium-7 in the CTFA Dictionary, is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the CTFA name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the CTFA name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10 in the CTFA Dictionary. Also useful are quaternized copolymers of hydroxyethylcellulose and dimethyldimethylammonium chloride, having the CTFA name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the CTFA names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the CTFA name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. Cocodimonium hydrolyzed animal protein, for example, is the CTFA name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

The total amount of the one or more conditioning agents, if present, may vary. In some cases, the total amount of the one or more conditioning agents is from about 0.1 to about 25 wt. %, about 0.1 to about 20 wt. %, about 0.1 to about 15 wt. %, 0.1 to about 10 wt. %, 0.1 to about 5 wt. %, about 1 to about 25 wt. %, about 1 to about 20 wt. %, about 1 to about 15 wt. %, about 1 to about 10 wt. %, or about 1 to about 5 wt. %, based on the total weight of the composition.

Thickening Agents

The compositions may contain one or more thickeners or viscosity modifying agents. Classes of such agents include, but are not limited to, viscous liquids, such as polyethylene glycol, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

The total amount of the one or more thickening agents may vary, but in some cases is about 0.1 to about 15 wt. %, about 0.1 to about 10 wt. %, about 0.1 to about 8 wt. %, about 0.1 to about 6 wt. %, about 0.1 to about 5 wt. %, about 0.5 to about 10 wt. %, about 0.5 to about 8 wt. %, about 0.5 to about wt. %, about 0.5 to about 5 wt. %, about 1 to about 10 wt. %, about 1 to about 8 wt. %, about 1 to about 6 wt. %, or about 1 to about 5 wt. %, based on the total weight of the composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldehyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Suitable components, such as those listed in the instant disclosure (including those listed above), may be included or excluded from the hair care formulations depending on the specific combination of other components, the form of the compositions, and/or the use of the formulation (e.g., hair spray, cream, conditioner, etc.).

Example Types of Compositions with Active Agents

Bleach Compositions

When hair lightening or color-altering compositions use separate bleach and developer compositions, the bleach composition may comprise at least one oxidizing agent chosen from persulfates, perborates, percarbonates, peracids, bromates, their salts, and mixtures thereof. In some instances, the at least one oxidizing agent is chosen from alkali metal salts of perborates, percarbonates, bromates, and persulfates, such as, for example, ammonium, sodium, and potassium salts. The bleach composition may also optionally comprise a cosmetically acceptable carrier.

The at least one oxidizing agent of the bleach compositions of the disclosure is utilized in an amount sufficient to lighten or "bleach" hair. By way of example only, the at least one oxidizing agent of the bleach composition may be present in an amount ranging from about 10% by weight to about 100% by weight, such as from about 20% to about 90% by weight, from about 30% to about 80% by weight, or from about 40% to about 75% by weight, based on the total weight of the bleach composition. In further embodiments, the at least one oxidizing agent of the bleach composition may be present in an amount ranging from about 5% to about 50%, such as about 10% to about 45%, or about 15% to about 40%. In some cases, the at least one oxidizing agent of the bleach composition may be present in an amount of at least 40% by weight, based on the total weight of the bleach composition.

The bleach composition may be in any form, such as, for example, in the form of a powder, gel, liquid, foam, lotion, cream, mousse, and emulsion.

In some cases, the bleach composition may be anhydrous. Optionally, water may be added as an activator, by mixing it with the bleach composition.

The bleach composition of the present disclosure may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the bleach composition in an amount effective to provide the color-altering composition with a pH ranging from about 1 to about 7 when the bleach composition is combined with the developer composition. By way of example, the amount of pH adjuster may be present, in various embodiments, in an amount of at least about 0.01%, such as at least about 0.1%, at least about 0.2%, or at least about 0.5%.

In some cases, the bleach composition is acidic, with the pH ranging from about 1 to about 7; and in some cases, the bleach composition has a pH higher than about 7. When the bleach composition is in powder form, the pH may be measured in a 1% solution in water.

Colorants may also optionally be present in the bleach compositions. The colorants useful according to various embodiments of the disclosure are those colorants that are stable in the bleach composition, and can impart additional toning and coloring to hair. Exemplary hair colorants include, but are not limited to, pigments, liposoluble dyes, direct dyes, nacreous pigments, pearling agents, leuco dyes, optical lightening colorants, natural colorants and optically-variable pigments.

Developer Compositions

Developer compositions often include peroxide, such as hydrogen peroxide. The developer composition may also optionally comprise a cosmetically acceptable carrier. The hydrogen peroxide may be present in an amount of at least about 1% by weight, based on the total weight of the developer composition. In some cases, hydrogen peroxide is present in an amount ranging from about 0.1% to about 80% by weight, such as from about 1.0% to about 75% by weight, or from about 2% to about 10% by weight, based on the total weight of the developer composition. Furthermore, the hydrogen peroxide may be present in the developer composition in an amount ranging from about 2% to about 25%, such as about 4% to about 20%, about 6% to about 15%, or about 7% to about 10%.

The cosmetically acceptable carrier of the developer composition may, for example, be present in an amount ranging from about 0.5% to about 99% by weight, such as from about 5% to about 95% by weight, relative to the total weight of the developer composition.

The pH of the developer composition can range from about 1 to about 5, such as from about 2 to about 4, and it may be adjusted to the desired value using pH adjusters that are well known in the art in the cosmetic treatment of keratin fibers, including, for example, those described herein.

The developer composition may be in the form of a powder, gel, liquid, foam, lotion, cream, mousse, and emulsion.

Optionally, water may be added as an activator, by mixing it with the developer composition.

The developer composition may, in various cases, comprise additional components such as, for example, at least one auxiliary ingredient chosen from rheology-modifying agents, chelants, fatty substances, ceramides, alkoxyaminosilicones, and silanes, and any other component known in the art to be useful in a developer composition.

In some instances, the bleach composition and developer composition may be combined to form the lightening composition or color-altering composition in a ratio of bleach composition to developer composition ranging from about 1:1 to about 1:5, such as from about 1:1 to about 1:2, or about 1:2 to about 1:4.

Shape-Altering Compositions

Compositions for altering the shape of the hair comprise hair shaping agents for example, agents for straightening, relaxing, and/or shaping the hair. By way of example, hair shaping agents may optionally be chosen from inorganic hydroxides or organic hydroxides, for example sodium hydroxide, potassium hydroxide, lithium hydroxide, calcium hydroxide, or guanidine hydroxide, or may be chosen from organic amines and other non-hydroxide compounds. In some cases, the hair shaping agents may be chosen from thiol compounds such as cysteine, cysteamine, N-substituted cysteamines, alkyl substituted mercaptoacetam ides, dimercaptoadipic acid, thioglycerol, thiolactic acid, thioglycolic acid or its salts, (e.g., a thioglycolate), monothioglycolic acid esters such as diol esters of thioglycolic acid, glyceryl monothioglycolate, thiocholine or its salts, amino thiols, and thiols attached to low molecular weight polymers, sulfites such as sodium hyposulfite, and bisulfites such as ammonium or sodium bisulfite.

The hair shaping composition may also comprise a cosmetically acceptable carrier. The cosmetically acceptable carrier may, for example, be present in the shape-altering composition in an amount ranging from about 1% to about 40% by weight, such as from about 5% to about 35% by weight, or about 10% to about 30% by weight of the shape-altering composition.

In some cases, the hair shaping composition comprises or is used in conjunction with at least one neutralizer (for example, in a neutralizing composition), for example an oxidizing agent. Exemplary useful oxidizing agents include peroxides, bromates, and perborates, e.g., hydrogen peroxide, potassium bromate, sodium bromate and sodium perborate.

The shape-altering composition may be left on the hair for a period of time sufficient to achieve the desired alteration in hair shape. For example, the shape-altering composition may be left on the hair for up to one hour, such as from about 3 minutes to about 45 minutes, from about 5 minutes to about 30 minutes, or from about 10 minutes to about 20 minutes. In further embodiments, the shape-altering composition may be left on the hair for a period up to about 30 minutes, such as, for example, from about 1 to about 30 minutes, about 1 to about 10 minutes, or about 1 to about 5 minutes. One skilled in the art will, by considering various factors such as starting hair shape and desired hair shape, be able to determine an appropriate amount of time to leave the shape-altering composition on the hair in order to achieve the desired alternation in hair shape.

If desired, the shape-altering composition may, optionally, be shampooed and/or rinsed off the hair.

Forms

The compositions described herein may be in any suitable physical form. Suitable forms include, but are not limited to low to moderate viscosity liquids, lotions, milks, mousses, sprays, gels, creams, conditioners, and the like.

i. Spray

The compositions described herein for treating hair may be in the form of a spray. The spray typically includes a cosmetically acceptable carrier. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant.

The hair spray formulations may be dispensed from containers that include aerosol dispensers or pump spray dispensers. Such dispensers are known in the art and are commercially available from a variety of manufacturers.

When the hair spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed.

The amount of propellant may range from about 10% to about 60% by weight of the formulation. The propellant may be separated from the hair repair formulation as in a two compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the hair strengthening formulation to the hair.

ii. Conditioners

The compositions disclosed herein may be in the form of a conditioner. The conditioner may include one or more conditioning agents, such as cationic surfactants (e.g., quaternary ammonium compounds, silicone compounds, oils, esters, and cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the compositions, and/or a conditioning action (deposition on the surface of the skin or the hair).

iii. Creams

The compositions disclosed herein for may be in the form of a cream. In some cases, when the compositions are in the form of a cream, the cream is an emulsion (e.g., water-in-oil or oil-in-water emulsion).

Implementation of the present disclosure is provided by way of the following examples. The examples serve to illustrate the technology without being limiting in nature.

Example 1

| (Formulations) | | | | |
|---|---|---|---|---|
| Claim Component | Ingredient | | #1 | #2 |
| (a) | Alkanolamine | Monoethanol Amine | 5.5 wt. % | |
| (a) | Diamine | 4,7,10-Trioxa-1,13-Tridecanediamine | | 20 wt. % |
| (b) | Unsaturated Carboxylic Acid | HEMA Maleate | 20 wt. % | 20 wt. % |
| (c) | Solvent | Ethanol | 74.5 wt. % | 60 wt. % |

Methacryloyloxyethyl maleate (HEMA Maleate) was combined with either monoethanol amine (MEA) or 4,7,10-trioxa-1,13-tridecanediamine (1:1 molar ratio) and dissolved in ethanol. Depending on the acid, amine, and solvent used, a precipitate may form.

Example 2

Cosmetic Properties 15 grams of a bleach powder was mixed with 15 grams of a developer composition, and 4 grams of Formulation 1 or Formulation 2 was added. Each of the two mixtures was separately applied to hair swatches for 35 minutes ("Regular Bleached Hair" obtained from HIP (International Hair Import Products)). After 35 minutes, the swatches were rinsed with water, shampooed once, and blown dry. The components of the bleach composition and the developer composition are provided below.

| Bleach Composition | |
|---|---|
| Ingredient | wt. % |
| Magnesium Carbonate Hydroxide | 9 |
| Sodium Silicate | 17 |
| Disodium EDTA | 1 |
| Sodium Metasilicate | 3 |
| Surfactants | 11 |
| Potassium Persulfate | 50 |

-continued

| | |
|---|---|
| Ammonium Persulfate | 5 |
| Additives and Optional Ingredients | 4 |

| Developer Compositions | | |
|---|---|---|
| Ingredient | wt. % | wt. % |
| Sodium Stannate | 0.04 | 0.04 |
| Surfactants | 3.7 | 3.7 |
| Pentasodium Pentetate | 0.06 | 0.06 |
| Glycerin | 0.5 | 0.5 |
| Hydrogen Peroxide | 9 | 12 |
| Tetrasodium Pyrophosphate | 0.02 | 0.02 |
| Water | QS 100 | QS 100 |

Hair swatches were treated similarly with compositions having no additive, control compositions, and benchmark compositions for comparison. The treated hair swatches were evaluated by three independent experts for sensorial characteristics (combability, smoothness, and discipline). Each individual expert ranked the hair swatches according to a four point scale, where "1" represents the best result and "4" represents the worst result. All three experts arrived at the same conclusions, which are shown below.

| | Smoothness | Dry Combability | Discipline |
|---|---|---|---|
| NoAdditive[1] | 3 | 3 | 3 |
| Control 1 (HEMA Maleate (20 wt. %)) | 4 | 4 | 4 |
| Control 2 (MEA (5.5 wt %)) | 2 | 2 | 3 |
| Control 3 (diamine (20 wt %)) | 2 | 2 | 3 |
| Commercial Benchmark 1[2] | 1 | 2 | 2 |
| Commercial Benchmark 2[2] | 1 | 2 | 2 |
| Formulation 1 | 1 | 1 | 1 |
| Formulation 2 | 1 | 1 | 1 |

[1]Hair bleached using only the combination of bleach powder and developer (1:1 ratio) (no maleic acid, no monoethanolamine, no maleic acid polymer).
[2]The commercial benchmarks include an amine and an unsaturated carboxylic acid, but the unsaturated carboxylic acid is different from the claimed unsaturated carboxylic acids of formula (I).

Hair bleached with no additive and hair treated with only an unsaturated carboxylic acid (component (b)) exhibited the worst cosmetic properties, as it was difficult to comb, it was rough, and exhibited the least amount of discipline. The addition of only an amine (monoethanol amine or 4,7,10-trioxa-1,13-tridecanediamine) (component (a)), as with Control 2 and 3, provided some improvement to cosmetic properties. However, the combination of a carboxylic acid (component (b)) with the monoethanol amine or 4,7,10-trioxa-1,13-tridecanediamine (component (a)) exhibited the very best results, as shown by Formulations 1 and 2.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat' (and its grammatical variations) as used herein also refers to contacting keratinous substrates such as hair with the compositions of the present disclosure.

A "rinse-off" product refers to a composition such as a hair care composition that is rinsed and/or washed with water either after or during the application of the composition onto the keratinous substrate, and before drying and/or styling said keratinous substrate. At least a portion of the composition is removed from the keratinous substrate during the rinsing and/or washing.

The term "stable" as used herein means that the composition does not exhibit phase separation and/or crystallization.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A restructuring composition comprising:
   (a) one or more amines selected from the group consisting of diamines, polyamines, alkylamines, alkanolamines, and mixtures thereof;
   (b) one or more unsaturated carboxylic acids of formula (I):

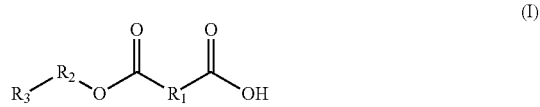

wherein $R_1$ is a linear or branched $C_2$-$C_{10}$ alkenyl group;
   $R_2$ is a linear or branched $C_1$-$C_{10}$ alkyl group; and
   $R_3$ is (meth)acryloyloxy; and
   (c) a cosmetically acceptable carrier;
   wherein the molar ratio of (a):(b) is about 0.1:1 to about 1:0.1.

2. The restructuring composition of claim 1 comprising one or more alkylamines and/or alkanolamines are selected from compounds of formula (II):

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl.

3. The restructuring composition of claim 2 comprising one or more alkanolamines selected from the group consisting of monoethanol amine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

4. The restructuring composition of claim 1 comprising one or more polyamines selected from the group consisting of a polyethyleneimine, a polyvinylamine, an aminated polysaccharide, an amine substituted polyalkylene glycol, an amine substituted polyacrylate crosspolymer, an amine substituted polyacrylate, an amine substituted polymethacrylate, an aminosilicone, a protein, an amine substituted polyester, a polyamino acid, an amodimethicone, a polyalkylamine, diethylene triamine, triethylenetetramine, spermidine, spermine, and mixtures thereof.

5. The restructuring composition of claim 1 comprising one or more diamine is selected from the group consisting of 3,6-dioxa-1,8-octanediamine, 4,7,10-trioxa-1,13-tridecanediamine, 4,7-dioxa-1,10-decanediamine, 4,9-dioxa-1,12-dodecanediamine, dimethyl aminopropyl amine, 1,6-hexane diamine, 1,3 propane diamine, 2-methyl 1,5 pentane diamine, 1,3-pentanediamine, 1,3-diaminobutane, 1,2-bis(2-aminoethoxy)ethane, isophorone diamine, 1,3-bis(methylamine)-cyclohexane and mixtures thereof.

6. The restructuring composition of claim 1 comprising:
(a) about 1 to about 25 wt. % of the one or more alkylamines and/or alkanolamines.

7. The restructuring composition of claim 1, wherein the one or more unsaturated carboxylic acids of formula (I) are selected from the group consisting of (meth)acryloyloxyethyl maleate, (meth)acryloyloxypropyl maleate, (meth)acryloyloxybutyl maleate, (meth)acryloyloxyethyl citraconate, (meth)acryloyloxypropyl citraconate, (meth)acryloyloxybutyl citraconate, (meth)acryloyloxyethyl dimethylmaleate, (meth)acryloyloxypropyl dimethylmaleate, (meth)acryloyloxybutyl dimethylmaleate, (meth)acryloyloxyethyl succinate, (meth)acryloyloxyethyl glutarate, (meth)allyloyloxyethyl maleate, and mixtures thereof.

8. The restructuring composition of claim 1 comprising:
(b) about 1 to about 50 wt. % of the one or more unsaturated carboxylic acids of formula (I).

9. A restructuring composition comprising:
(a) about 1 to about 25 wt. % of monoethanolamine;
(b) about 1 to about 50 wt. % of (meth)acryloyloxyethyl maleate; and
(c) about 30 to about 90 wt. % of cosmetically acceptable carrier;
wherein the molar ratio of (a):(b) is about 0.4:1 to about 1:0.4.

10. A composition for chemically treating hair comprising:
(a) one or more alkylamines and/or alkanolamines;
(b) one or more unsaturated carboxylic acids of formula (I):

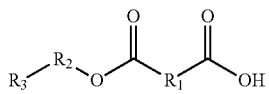

wherein $R_1$ is a linear or branched $C_2$-$C_{10}$ alkenyl group;
$R_2$ is a linear or branched $C_1$-$C_{10}$ alkyl group; and
$R_3$ is (meth)acryloyloxy; and
(c) one or more active agents selected from the group consisting of oxidizing agents, reducing agents, non-reducing agents for shaping hair, dyeing agents, and mixtures thereof.

11. A composition of claim 10 that is a hair lightening composition comprising one or more oxidizing agents selected from the group consisting of one or more peroxides, persulfates, perborates, percarbonates, and mixtures thereof.

12. A composition of claim 10 selected from the group consisting of:
(i) a hair lightening composition comprising one or more oxidizing agents selected from the group consisting of one or more peroxides, persulfates, perborates, percarbonates, and mixtures thereof;
(ii) a hair perming or straightening composition comprising one or more reducing agents selected from the group consisting of cysteine or a derivative of cysteine, cysteamine or a derivative of cysteamine, thiolactic acid or an ester of thiolactic acid, thioglycolic acid or an ester of thioglycolic acid, thioglycerol, and mixtures thereof;
(iii) a hair straightening or relaxing composition comprising one or more non-reducing agents for shaping hair selected from the group consisting of hydroxide compounds, non-hydroxide compounds, and mixtures thereof; and
(iv) a hair-coloring composition comprising one or more dyeing agents selected from the group consisting of direct dyes, oxidative dyes, direct action dyes, natural dyes, metallic dyes, reactive dyes, and mixtures thereof.

13. A method for restructuring hair comprising applying to the hair a restructuring composition of claim 1.

14. A method for chemically treating hair comprising:
i. applying to the hair a composition for chemically treating the hair of claim 10;
ii. allowing the composition to remain on the hair for about 1 to about 45 minutes; and
iii. rinsing the composition from hair.

15. A kit comprising:
i. a restructuring composition of claim 1;
ii. a composition comprising one or more active agents for chemically treating hair; and
iii. optionally, a composition comprising one or more hair conditioning agents.

16. A kit comprising:
i. a composition for chemically treating hair of claim 10; and
ii. a composition comprising one or more second active agents that is different than the one or more active agents in (i); and
iii. optionally, a composition comprising one or more hair conditioning agents.

17. A method for making the restructuring composition of claim 1 comprising combining in a solvent, one or more amines selected from the group consisting of diamines, polyamines, alkylamines, alkanolamines, and mixtures thereof with one or more unsaturated carboxylic acids of formula (I)

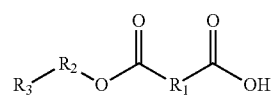

wherein $R_1$ is a linear or branched $C_2$-$C_{10}$ alkenyl group;
$R_2$ is a linear or branched $C_1$-$C_{10}$ alkyl group; and
$R_3$ is (meth)acryloyloxy.

18. A cosmetic Michael adduct formed in situ during a hair-care treatment, the cosmetic Michael adduct being formed by combining:
(a) an amine selected from the group consisting of diamines, polyamines, alkylamines, and alkanolamines; with
(b) an unsaturated carboxylic acids of formula (I):

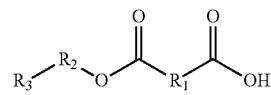

wherein $R_1$ is a linear or branched $C_2$-$C_{10}$ alkenyl group;
$R_2$ is a linear or branched $C_1$-$C_{10}$ alkyl group; and
$R_3$ is (meth)acryloyloxy.

* * * * *